(12) United States Patent
Poglitsch et al.

(10) Patent No.: US 7,714,304 B2
(45) Date of Patent: May 11, 2010

(54) COMPUTED TOMOGRAPHY MEASURING ARRANGEMENT AND METHOD

(75) Inventors: Christof Poglitsch, Aalen (DE); Ronald Lonardoni, Westhausen (DE)

(73) Assignee: Carl Zeiss Industrielle Messtechnik GmbH, Oberkocken (DE)

( * ) Notice: Subject to any disclaimer, the term of this patent is extended or adjusted under 35 U.S.C. 154(b) by 108 days.

(21) Appl. No.: 12/064,104

(22) PCT Filed: Aug. 15, 2006

(86) PCT No.: PCT/EP2006/008134

§ 371 (c)(1),
(2), (4) Date: Feb. 19, 2008

(87) PCT Pub. No.: WO2007/020095

PCT Pub. Date: Feb. 22, 2007

(65) Prior Publication Data

US 2008/0217559 A1    Sep. 11, 2008

(30) Foreign Application Priority Data

Aug. 16, 2005    (DE) .................. 10 2005 039 422

(51) Int. Cl.
*G01N 23/00*    (2006.01)
*A61B 6/00*    (2006.01)
(52) U.S. Cl. .............................. 250/491.1; 250/370.09; 378/20; 378/125; 378/144
(58) Field of Classification Search .............. 250/370.1, 250/370.08, 370.09, 491.1, 492.1, 492.22; 378/4, 8, 10, 17, 19–21, 24, 27, 62, 125, 378/143, 144, 210, 910
See application file for complete search history.

(56) References Cited

U.S. PATENT DOCUMENTS 4,422,177 A    12/1983    Mastronardi et al.

(Continued)

FOREIGN PATENT DOCUMENTS

DE    3924066 A1    2/1990

(Continued)

OTHER PUBLICATIONS

Kang et al. "A projection method for reconstruction X-ray images of arbitrary cross-section",NDT&E International, Butterworth-Heinemann, Oxford, GB vol. 32, No. 1, Jan. 1999, pp. 9-20, figure 12, ISSN: 0963-8695, XP004292640.

(Continued)

*Primary Examiner*—Bernard E Souw
(74) *Attorney, Agent, or Firm*—Laurence A Greenberg; Werner H Stemer; Ralph E Locher

(57) ABSTRACT

A computer tomography measuring device includes a radiation source for generating invasive radiation, in particular X-rays, and a rotating device which is embodied and arranged in such a way that it enables a measurement object to be rotatable about an axis of rotation of the rotating device, thereby enabling the invasive radiation to penetrate into the measurement object at different angles. A detecting device detects the radiation penetrating through the measurement object. A positioning device provided with an adjusting element is used for adjusting the position of the measurement object with respect to the rotating device.

15 Claims, 2 Drawing Sheets

U.S. PATENT DOCUMENTS

| | | | | |
|---|---|---|---|---|
| 4,969,110 | A * | 11/1990 | Little et al. | 382/131 |
| 5,023,895 | A * | 6/1991 | McCroskey et al. | 378/4 |
| 5,119,408 | A | 6/1992 | Little et al. | |
| 5,222,114 | A | 6/1993 | Kamata et al. | |
| 5,228,071 | A | 7/1993 | Kamata et al. | |
| 5,383,119 | A * | 1/1995 | Tam | 378/8 |
| 6,525,875 | B1 * | 2/2003 | Lauer | 359/371 |
| 7,505,550 | B2 * | 3/2009 | Goto et al. | 378/4 |
| 2003/0164842 | A1 * | 9/2003 | Oberoi et al. | 345/629 |
| 2004/0213378 | A1 * | 10/2004 | Zhou et al. | 378/122 |
| 2005/0041771 | A1 * | 2/2005 | Kuo-Petravic et al. | 378/19 |
| 2007/0041491 | A1 * | 2/2007 | Sadakane et al. | 378/15 |
| 2007/0189436 | A1 * | 8/2007 | Goto et al. | 378/4 |
| 2008/0137802 | A1 * | 6/2008 | Suzuki et al. | 378/4 |
| 2008/0159470 | A1 * | 7/2008 | Sadotomo et al. | 378/15 |
| 2008/0217559 | A1 * | 9/2008 | Poglitsch et al. | 250/491.1 |

FOREIGN PATENT DOCUMENTS

EP        0461776  A2    12/1991

OTHER PUBLICATIONS

International Search Report dated December 21, 2006.

* cited by examiner

COMPUTED TOMOGRAPHY MEASURING ARRANGEMENT AND METHOD

BACKGROUND OF THE INVENTION

Field of the Invention

The invention relates to a computed tomography (CT) measuring arrangement that generates radiation images (and therefrom, in particular, volume images and/or measured volume data) of measurement objects by means of invasive radiation, e.g. an X-ray CT measuring arrangement. The invention further relates to a method for carrying out computed tomography, in particular a method for preparing a computed tomography measurement.

The use of invasive radiation for examining workpieces is known. In computed tomography (CT), the workpiece is, for example, generally arranged on a rotary table and transradiated with X-radiation from various directions by rotating the rotary table into various rotary positions. The radiation attenuated by extinction in the material of the workpiece is detected by a sensor device in a spatially and temporally resolved fashion. In practice, between 800 and 1200 projection images of the measurement object are recorded by way of example, the rotary position being varied by a rotary angle of constant magnitude between each of the projections. A three-dimensional image of the workpiece is calculated therefrom by applying one of a number of known methods of tomographic reconstruction, for example filtered back projection. The 3D image respectively specifies the local linear adsorption coefficient for individual small volume elements (voxels). An example for CT is described in DE 39 24 066 A1.

In the case of central projections, which emanate from a virtually punctiform radiation source, the imaging quality in the recording of projection images is a function, in particular, of the selected magnification, that is to say of how large is the region of the radiation that impinges on the detection device and has penetrated the measurement object.

The user of such a CT measuring arrangement therefore has to ensure that the measurement object respectively produces as large a projection image as possible before and after rotations about the axis of rotation of the rotary table, and that in the process the measurement object is respectively imaged completely onto the detection surface of the detection device.

A corresponding positioning of the measurement object is usually carried out manually: after the measurement object has been correctly positioned in a specific rotary position, it is positioned in turn in another rotary position. An iterative process frequently results in this case. The outlay on this is yet further increased by virtue of the fact that personnel protection measures are taken in the case of measuring arrangements with the aid of X-radiation. For example, there is a need in each case for a measuring cabin to be opened before the positioning and to be closed again after the positioning.

BRIEF SUMMARY OF THE INVENTION

It is an object of the present invention to specify a method and a measuring arrangement that enable projection images as large as possible to be obtained in the case of CT measuring arrangements, the outlay on positioning the measurement object being intended to be low.

It is proposed to use a positioning device by means of which the measurement object can be positioned in the measuring arrangement. In particular, a measuring arrangement for computed tomography (CT) is proposed that has the following:

a radiation source for generating an invasive radiation, in particular X-radiation, a rotating device that is configured and arranged in such a way that a measurement object can be rotated about an axis of rotation of the rotating device, and that in this way the invasive radiation can penetrate the measurement object from various directions, and a detection device for detecting radiation that has penetrated the measurement object, characterized by a positioning device, the positioning device having a setting device that is configured to set a position of the measurement object relative to the rotating device.

By contrast with measuring arrangements for medical purposes, the measuring arrangement serves the purpose, in particular, of measuring a measurement object produced manually and/or industrially. In particular, the measuring station at which the measurement object is to be arranged during measurement is of corresponding configuration. Alternatively, or in addition, the positioning device is configured only for positioning inanimate objects. For example, the positioning device can have a holder for holding the object that preferably clamps the measurement object. Consequently, the measurement object can be fixed relative to the holder in a permanent and reproducible fashion.

The term invasive radiation includes radiation of any type that penetrates the measurement object. Apart from electromagnetic radiation—such as X-radiation for example—it is also possible to use particle radiation (for example electron radiation or positron radiation). Again, electromagnetic radiation in other wavelength regions (for example in the visible or infrared wavelength region) can be used. Apart from the actual measuring radiation, radiation from secondary effects (such as excitation of energy states, for example luminescence) or scattered radiation is frequently also detected. Such radiation is usually present as "background" or noise in the measurement signals.

In a preferred type of examination of the measurement object, use is made of electromagnetic radiation that penetrates the measurement object and is detected on the opposite side of the radiation source from the spatially resolving sensor device. In particular, the measuring arrangement is configured such that the invasive radiation produced by the radiation source penetrates the measurement object and generates a projection image in a type of central projection.

Furthermore, it is preferred for the electromagnetic radiation to be X-radiation or gamma radiation (hard X-radiation) that lies in the energy range from 0.5 keV to 50 MeV. X-radiation in the energy range from 2 keV to 700 keV is particularly preferred.

When use is made of X-ray sources with a small focal spot, the source of the invasive radiation can be taken to be virtually punctiform. Such a measuring arrangement with a virtually punctiform radiation source is likewise particularly preferred. Use is made, for example, of an X-ray source with a focal spot diameter in the range of 5 to 100 micrometers. As a rule, sources of this type generate polychromatic X-radiation, for example in the energy range of 10 to 450 keV. With regard to the distance from the measurement object, which is generally substantially greater by comparison with the focal spot diameter, and from the detection device (of the order of magnitude of a few tens of centimeters to more than 1 meter), the focal spot can be designated as punctiform. The images recorded with the detection device (or the corresponding image data) contain information on the intensity of the X-radiation that has traversed the measurement object. The so-called cumulative absorption coefficient can be calculated from this information in a way known per se for each pixel of the image. On the basis of the punctiform radiation source, the images thus obtained correspond to central projections (the projection center coinciding with the radiation source) of a material property (the local extinction coefficient) of the measurement object, since the invasive radiation emitted by the radiation source forms a diverging radiation beam.

In particular, the invention can advantageously be applied when the radiation image corresponds to a measurement geometry that generates the radiation image by a central projection emanating from a punctiform radiation source. Here, the term "corresponds" signifies that the radiation image has really been generated by a central projection, or that the radiation image (for example through deviation of the invasive radiation before and/or after the transradiation of the object, for example by collimators and/or lenses) was generated by a measuring arrangement that generates radiation images identical to a central projection. What is understood by a central projection is that the path of each ray of the invasive radiation from the punctiform radiation source up to the detection device is a straight line. A radiation source is designated as punctiform whenever the production region of the radiation or a region that must be traversed by all radiation used for the projection is so small in view of the overall geometry of the measuring arrangement that the region can be regarded as approximately punctiform.

In particular, the radiation source is configured to generate a conical diverging radiation beam that is emitted in the direction of the detection device. Here, the quality (or at least the outlay for a correction) of the reconstruction result, which is obtained from the projection images recorded in the various rotary positions, is a function of how exactly a ray which is central with reference to the conical radiation beam crosses the axis of rotation of the rotating device in a perpendicular fashion. Such a perpendicular crossing is preferably substantially achieved.

The positioning device is now preferably used to position the measurement object (to center it with reference to the axis of rotation) such that the axis of rotation is the common line of two cutting planes of the measurement object that run perpendicular to one another, the axis of rotation running in the two cutting planes in the middle between opposite outer edges and/or outer surface points of the measurement object.

This goal (or else any other positioning of the measurement object) can be achieved in a simple way and, moreover, with high accuracy by means of the setting device, which can set the position of the measurement object relative to the rotating device. The user of the measuring arrangement no longer needs to set the position by hand, given that he is displacing the object on a rotary table. In particular, it is now possible for this position to be reset reproducibly, and/or to carry out a predefined variation of the position. A one- or multidimensional coordinate system is preferably defined for the positioning device or at least for a control device for controlling the setting device, or at least a scaling is provided such that coordinates or scaling values can be prescribed for a position and/or for a change in position, and the setting device can set the corresponding position, or can carry out the corresponding change in position.

Three different methods, which are described below and are designated as "only manual", "semiautomatic" and "fully automatic" are conceivable for setting the position of the measurement object with the aid of the positioning device. In all three cases, the measurement object is preferably permanently connected to a part of the positioning device, for example, clamped in the positioning device, for example in the manner of a vise, or the measurement object varies its relative position in relation to the part of the position of the device for other reasons and in an unintentional fashion (for example because it is permanently on the part). However, other refinements are also possible, for example the use of stops that bear against a surface region of the measurement object, at least one stop being movable and the position of the stop and/or the orientation thereof being capable of varying relative to the rotating device.

In the case of purely manual setting of the position, the setting device is actuated by hand, for example by turning a thread rod.

In the case of the semiautomatic setting of the position, it is possible, for example, to provide a motor that varies the position of a moveable part of the setting device, and thus the measurement object. However, the motor is operated by a user. However, a motor has the advantage that a control device can be provided, for example. For example, the user need therefore prescribe only coordinates or difference coordinates for the control device, and the appropriate position or change in position is set automatically.

In the case of the fully automatic setting of the position, a position error (defined as a deviation of an actual position of the measurement object from a prescribed position) is automatically detected, and a corresponding position correction is undertaken. Once again, one or more of the motors can be provided in the case of the setting device. In particular, an image detection and processing method can be applied to detect a position error. An image of the measurement object is detected to this end by the detection device of the measuring arrangement. An image is generated from the detection signals in a following step. It can now be predefined at which point of the image the image values (for example gray-scale values from the evaluation of an X-radiation projection image of the measurement object) may undershoot or overshoot a specific limiting value. Consequently, it is possible to determine, particularly by considering an expected image of the measurement object with the aid of planning data (for example CAD planning data), whether the measurement object is centered in the instantaneous rotary position with reference to the axis of rotation and/or with reference to the region that can be detected by the detection device. The desired position can thus, in particular, be defined by virtue of the fact that the outer boundaries in the image of the measurement object are located on both sides of the axis of rotation at the same distance from the axis of rotation. Consequently, it is preferably determined before or during evaluation of the image which (virtual) line in the image corresponds to a projection of the axis of rotation. The information thereon can be obtained from calibration methods known per se. In more general terms, a projection image, generated from detection signals of the detection device, of the measurement object can be evaluated, and a positioning error of the measurement object can be determined from the projection image.

The detection and evaluation of images cannot only be carried out in the case of the fully automatic method, but can also, for example, be a basis for the semiautomatic method. If a control device for controlling the setting device is used either in the semiautomatic method or in the fully automatic method, or if such a control device is provided in the case of the measuring arrangement, the control device is preferably part of a control unit of the overall measuring arrangement. The control device can, for example, be implemented by software and/or hardware of a control computer of the measuring arrangement.

The setting device preferably has at least one positioning unit that is configured to set the position of the measurement object only along a rectilinear axis. It is possible thereby to carry out a targeted correction that is independent of other position errors.

It is particularly preferred that the setting device has at least two and preferably three of the positioning units, with the rectilinear axes of the positioning units running transversely and preferably at right angles to one another.

The setting device can be electrically, actuated, at least one electric line having for the purpose of supplying the setting device with electric current an electric connection that connects a first part of the line, which is arranged in and/or on the rotating device, to a second part of the line, which is arranged in and/or on the positioning device. A compact design is possible in this way without disturbing, exposed electric lines. In particular, it is thus also possible to avoid measurement artefacts that can be generated in the image by the material of such lines.

The setting device can preferably be electrically actuated, at least one electric line being provided for the purpose of supplying the setting device with electric current, the electric line leading via at least one electric sliding contact that in the event of an existing electric contact permits a movement of at least one part of the positioning device relative to another part of the positioning device and/or relative to the rotating device.

A further aspect of the invention relates to the determination of the present position and/or alignment of the measurement object in the measuring arrangement. It is proposed to use radiation (electromagnetic radiation and/or particle radiation) for determining the present position. On the one hand, it is also possible to use the type of radiation generated by the radiation source of the measuring arrangement during the actual measurement. For example, the radiation source is operated in a separate position measurement, and a projection image of the measurement object is produced by the detection device of the measuring arrangement. The image information thus obtained can, for example, be used for determining position in the above-described fully automatic variant of the method.

Alternatively or additionally, it is proposed to use a second radiation source in addition to the actual radiation source of the measuring arrangement. This second radiation source can, for example, generate radiation that propagates on its way to the measurement object in a fashion parallel to the radiation that would be generated by the first radiation source during the actual measurement of the measurement object. In other words, a central axis of the radiation generated by the second radiation source can extend parallel to a central axis (for example the axis of the beam cone) of the radiation generated by the first radiation source during the normal measurement operation. The corresponding offset (or another offset of the radiation on the basis of the fact that the second radiation source is not located at the site of the first radiation source) can be considered during evaluation.

A second possibility of compensating an offset is to use a plurality of second radiation sources that are positioned and aligned symmetrically with reference to the detection device and with reference to the central axis of the radiation generated by the first radiation source. For example, two of the second radiation sources are positioned to the right and left at the same distance from the first radiation source. These second radiation sources enable a projection image of the measurement object to be produced on the detection device or on an additional, second detection device that is, for example, arranged in front of the first detection device and is sensitive to the radiation of the second radiation sources.

A further possibility for using a second radiation source is to couple the radiation generated by the second radiation source into the beam path that is used by the first radiation during the actual measurement of the measurement object. It is possible to make use to this end of, for example, lenses, lens systems and/or other means (for example electromagnetic fields) in order to influence the direction of radiation. Also belonging here are mirrors and other reflecting components that utilize the effect of total reflection, for example.

Yet a further possibility for using a second radiation source consists in that the second radiation source is arranged in the beam path of the first radiation between the first radiation source and the detection device. It is possible here, in turn, to make optional use of the said means for influencing the direction of the propagating radiation, for example. A radiation beam is preferably thus generated whose geometry and propagation direction correspond as exactly as possible to the radiation generated by the first radiation source.

It is preferred to produce a projection image of the measurement object by utilizing the second radiation generated by the second radiation source(s). For example, as already explained above a second detection device is provided to this end and is arranged, for example, immediately in front of the first detection device and can optionally be removed again after the positioning of the measurement object. However, it is also conceivable to configure the first detection device to be both sensitive to the first radiation and sensitive to the second radiation.

The second radiation can, in particular, be visible radiation, which is thus completely safe for the user. This is based on the finding that it suffices for positioning to produce a pure shadow image of the measurement object, that is to say an image in the case of which no radiation of any type penetrates through the measurement object.

It is preferred to undertake a complete positioning of the measurement object, that is to say a positioning in at least two different rotary positions (for example rotary positions rotated by 90° relative to one another).

Consideration is given as second radiation source to, for example, a mercury vapor lamp, a halogen lamp, an inert gas lamp (for example a xenon lamp) and/or a laser. When use is made of a laser, it is possible as an alternative to directly determine the position of specific outer contours of the measurement object relative to the detection device when the laser beam is not expanded. It is preferred in this case to determine a multiplicity of the positions. However, it is also possible to expand the laser beam, and so to generate a diverging radiation beam as in the case of other radiation sources.

Moreover, a method is proposed for carrying out computed tomography (CT), in particular a method for preparing the recording of images of the measurement object. During recording, the measurement object is transradiated by invasive radiation, in particular X-radiation, in various rotary positions with reference to an axis of rotation, and at least one radiation image is recorded in each case. In order to prepare the recording, a relative position of the measurement object is varied relative to the axis of rotation by setting a positioning device. In particular, the measurement object can thereby be centered relative to the axis of rotation before the recording of the radiation images. It is understood by centering that, at least in a cutting plane through the measurement object, the cutting plane containing the axis of rotation, the points, lying farthest removed from the axis of rotation, of the outer contours of the measurement object lie on both sides of the axis of rotation equally far from the axis of rotation. Such a centering is preferably carried out with reference to two of the cutting planes, the two cutting planes running transverse to one another, in particular at right angles to one another. It is possible in this way to achieve optimum utilization of the available detection surface, and thus to attain the maximum magnification.

In particular, as described above and will be further described with reference to the attached drawing, the positioning device can be a positioning device that has at least one first part that is arranged in a stationary fashion relative to the axis of rotation. Other parts of the positioning device can be moved relative to this part, and so the measurement object likewise moves relative to the axis of rotation. The positioning device can be supported by the first part, for example, on the abovementioned rotating device.

In a preferred refinement of the method, radiation images of the measurement object are evaluated in advance, the measurement object already being arranged in the measuring arrangement. The actual radiation images are generated from detection signals of a detection device. At least one preliminary radiation image of the measurement object is evaluated before the recording of the radiation images, which are to be evaluated in order to examine the measurement object, from the detection signals, and a positioning error of the measurement object is determined from the preliminary radiation image.

In particular, the preliminary radiation image can be used in the following way: an image position of the axis of rotation that corresponds to a radiation projection (during the projection, the radiation covers, for example, an entirely rectilinear path from the radiation source through the measurement object and up to the detection device) of the axis of rotation onto the detection device is determined in the preliminary radiation image. The accurate position and alignment of the projection of the axis of rotation are known (for example in pixel coordinates of the detection device) from a calibration of the measuring arrangement, for example. It is now determined by evaluating the preliminary radiation image whether points, lying farthest removed from the axis of rotation in an image plane of the preliminary radiation image, of outer contours of the measurement object are located on both sides of the axis of rotation equally far from the axis of rotation. Such a positioning error is preferably corrected automatically.

For example, the position of the measurement object is automatically corrected by controlling the positioning device when the points, lying farthest removed, of the outer contours of the measurement object are located on the two sides of the axis of rotation unequally far from the axis of rotation.

The invention is explained in more detail below with the aid of exemplary embodiments that are illustrated schematically in the figures. However, the invention is not restricted to the examples. Identical reference symbols in the individual figures denote in this case elements that are identical or functionally identical or correspond to one another with regard to their functions. In the individual figures of the drawing,

DESCRIPTION OF THE INVENTION

Figure 1:
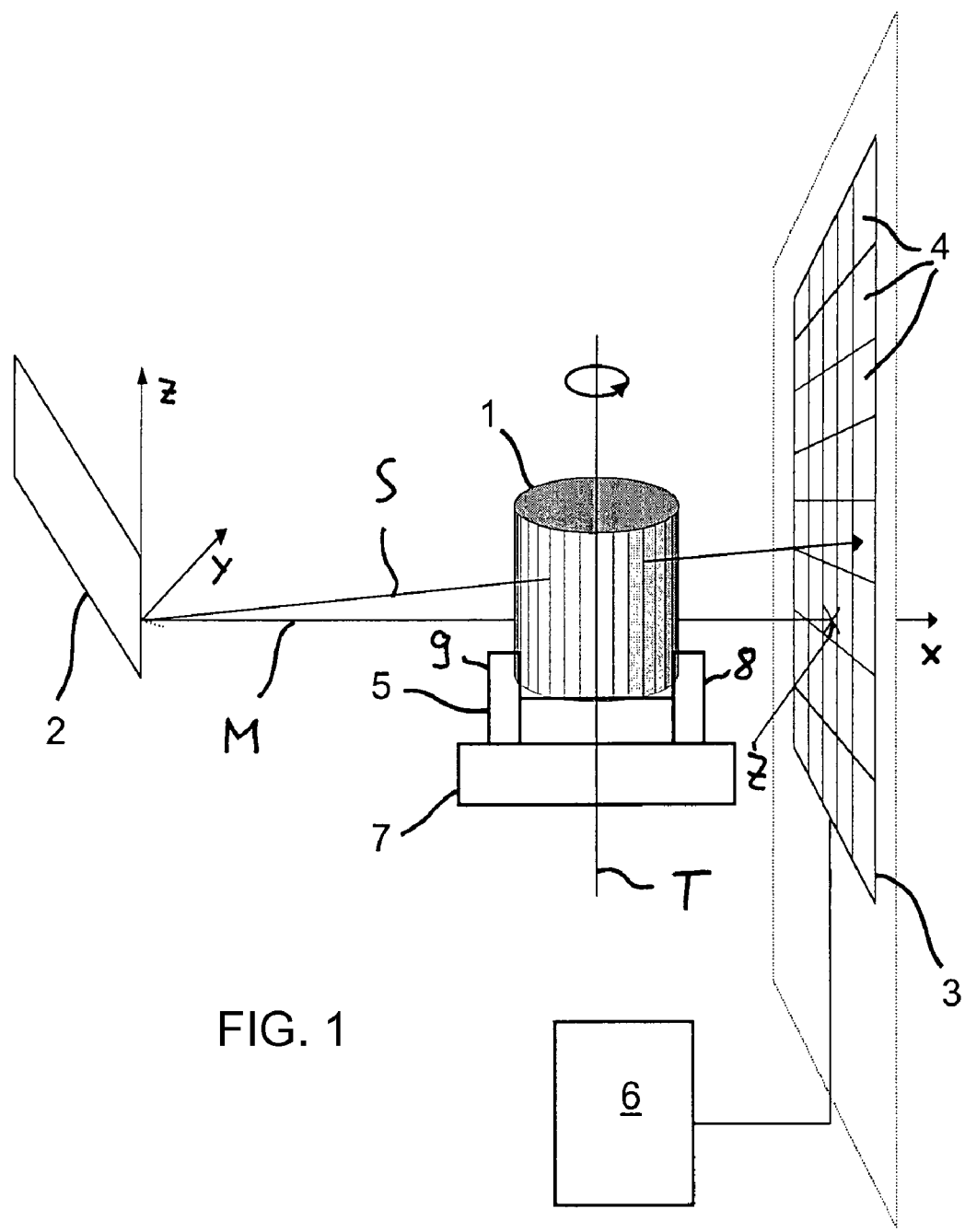
FIG. 1 is a schematic of a measuring arrangement with the aid of which measurement objects can be examined by means of invasive radiation.

The measuring arrangement illustrated in FIG. 1 has a measurement object 1 that is arranged in the rectilinear beam path between a radiation source 2, in particular an X-ray source, and a detection device 3. The detection device 3 has a multiplicity of detection elements 4 such that a spatially resolved detection of radiation is possible. The detection signals of the detection elements 4 are led to an evaluation device 6 that determines a radiation image of the measurement object 1 in a respectively given rotary position of the measurement object 1. The measurement object 1 is combined with a rotating device 7, for example a rotary table. The axis of rotation of the rotating device 7 is denoted by T. Also provided is a positioning device 5 that enables the measurement object 1 to be positioned relative to the rotating device.

The positioning device 5 is preferably configured such that it separately enables the positioning of the measurement object 1 in the direction of three coordinate axes of a Cartesian coordinate system. It is thereby possible to correct faulty positioning of the measurement object 1 by linear movement in the direction, in each case, of the individual coordinate axes. Alternatively or additionally, the positioning device 5 can enable further positioning movements, for example rotation movements about an axis of rotation that does not coincide with the axis of rotation T of the rotating device 7. Again, by way of example, it is thus possible to correct instances of tilting of the measurement object relative to a surface of the rotary table.

In particular, as illustrated schematically in the exemplary embodiment of FIG. 1, the positioning device 5 is arranged between the surface of the rotating device 7 (for example the rotary table surface) and an underside of the measurement object 1. However, other arrangements are also conceivable. For example, the measurement object can be gripped by an element of the positioning device and extend away laterally from the positioning device.

As is indicated in FIG. 1 by two lateral clamping jaws 8, 9 of the positioning device 5, the measurement object 1 can be clamped in the positioning device 5. However, it is also possible for the measurement object to be arranged in another way on the positioning device. For example, the measurement object can merely be placed onto a placement surface of the positioning device (see FIG. 3, for example).

A Cartesian coordinate system of the measuring arrangement is illustrated in FIG. 1. The x-axis extends from the radiation source 2, which is punctiform to a good approximation (for example the focal spot of the radiation source), through the measuring station, on which the measurement object can be arranged, and up to the detection device 3. A ray M, running exactly along the x-axis, of the invasive radiation generated by the radiation source 2 penetrates the detection device 3 at a penetration point Z, strikes a corresponding detection element and is detected there.

The detection device 3 is preferably a device with a flat detection surface on which the radiation to be detected impinges, the flat detection surface being perpendicular to the x-axis. The axis of rotation T of the rotating device 7 is usually adjusted such that it runs perpendicular to the x-axis. Moreover, adjustment is performed in such a way that the x-axis is the central axis of a radiation cone generated by the radiation source 2. A further ray of the radiation cone is denoted in FIG. 1 by the reference symbol S.

The y-axis of the coordinate system of the measuring arrangement extends parallel to the detection plane of the detection device 3, specifically in a horizontal direction. The z-axis of the coordinate system likewise extends parallel to the detection plane and preferably also parallel to the axis of rotation T.

Figure 2:
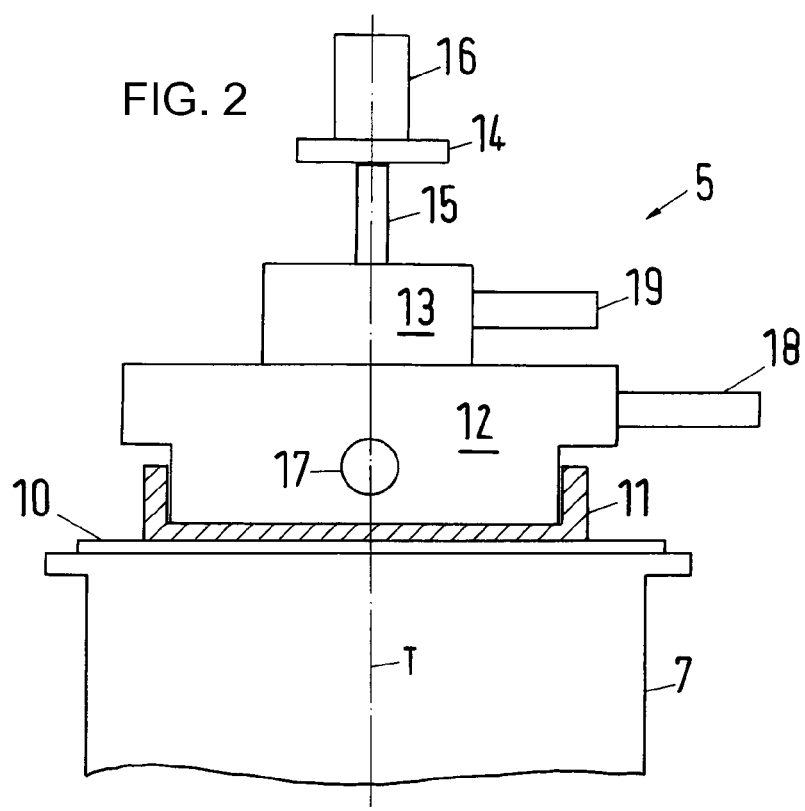
FIG. 2 is a schematic side view of an arrangement having a rotary table and a positioning device arranged thereon.
Figure 3:
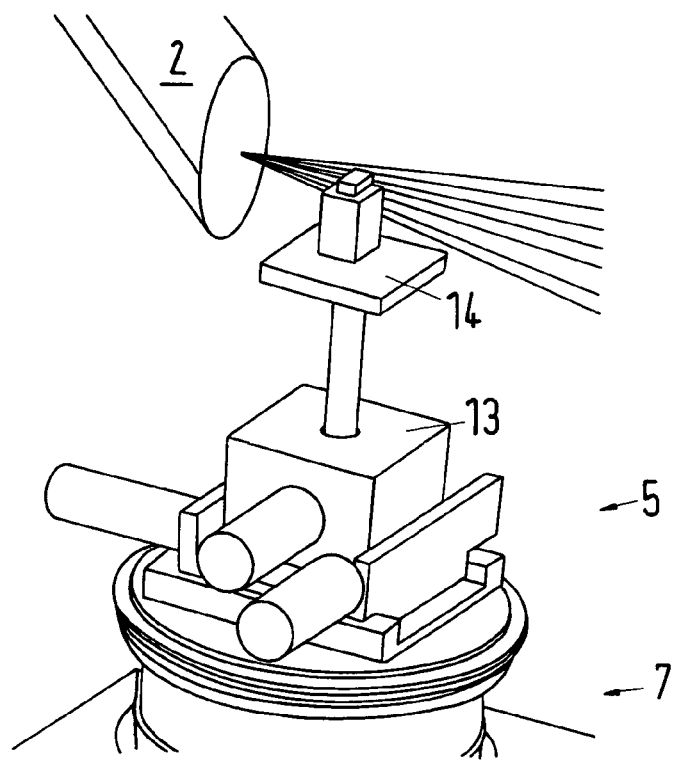
FIG. 3 shows the arrangement in accordance with FIG. 2 in a perspective illustration, a measurement object and an X-ray source additionally being illustrated.

FIG. 2 and FIG. 3 show a preferred embodiment of a positioning device that is likewise denoted by the reference symbol 5. A rotary table 7 with the axis of rotation T is to be seen at the bottom in the side view in accordance with FIG. 2. The positioning device 5 is arranged on the table surface 10. The positioning device 5 has a base element 11 that has a U-shaped profile. A first moveable element 12 can be moved in rectilinear fashion relative to the base element 11, specifically preferably by actuating a motor 17 that actuates a setting mechanism via a screw. In the illustration of FIG. 2, the axis of the relative movement between the first moveable element 12 and the base element 11 runs perpendicular to the plane of the drawing.

The positioning device 5 has a second moveable element 13, which can be moved relative to the first moveable element 12, specifically in rectilinear fashion along a movement axis whose movement direction runs perpendicular to the movement direction of the first moveable element 12. In the illustration of FIG. 2, the second movement direction runs horizontally in the image plane. Provided for actuating the movement is a second motor 18 which, for example, actuates a corresponding movement mechanism, once again via a screw.

Furthermore, a third moveable element 14 is provided, being configured, in particular, as a plate-shaped element. A type of sample table or measurement object table is yielded in this way. The third moveable element 14 is moveably connected to the second moveable element 13 via an elongated support 15 extending substantially in a vertical direction.

The third moveable element 14 and the support 15 permit a rectilinear movement relative to the second moveable element 13. In the illustration of FIG. 2, the axis of the movement runs in a vertical direction and lies in the image plane. A third motor 19 is arranged on the second moveable element 13 and actuates the movement of the third moveable element 14.

Denoted by 16 in FIG. 2 is an element that can be placed onto the surface of the third moveable element 14 in order to raise the position of the measurement object (not illustrated in FIG. 2, see FIG. 3). Larger measurement objects can, however, also be placed directly onto the third moveable element 14, for example.

For example, the positioning device is configured such that the position of the measurement object can be adjusted by 150 to 200 mm, for example by 160 mm, for example in the two horizontal directions perpendicular to one another (adjustable by moving the first moveable element 12 and second moveable element 13 relative to the rotary table).

Furthermore, the positioning device 5 is configured, for example, such that the measurement object can be adjusted by 15 to 25 mm, for example by 20 mm, in a vertical direction (by moving the third moveable element 14).

In a more general formulation, it should be possible to adjust the measurement object with reference to the coordinate system of the measuring arrangement (see FIG. 1) in the y-direction and in the z-direction by approximately half the width or height, respectively, of the extent of that region in which the detection device can receive and detect radiation. In this case, the detection device can be, for example, a device arranged in a stationary fashion and having a detection surface, or it can alternatively be a scanning sensor.

The positioning device is preferably designed to be as small and compact as possible in order to minimize the effect of geometric errors and instances of lack of rigidity of the device on the result of the image examination.

The invention claimed is:

1. A measuring arrangement for computed tomography, the measuring arrangement comprising:
 a radiation source for generating invasive radiation;
 a rotating device configured and disposed to enable a measurement object to be rotated about an axis of rotation of the rotating device, to cause the invasive radiation to penetrate the measurement object in a variety of directions;
 a detection device for detecting radiation after penetration through the measurement object;
 a positioning device, said positioning device having a setting device configured to set a position of the measurement object relative to said rotating device;
 the measuring arrangement being configured to:
   a) generate at least one preliminary radiation image of the measurement object from detection signals of said detection device;
   b) determine, from the preliminary radiation image, an image position of the axis of rotation corresponding to a radiation projection of the axis of rotation onto said detection device; and
   c) determine, by evaluating the at least one preliminary radiation image, whether or not, in one image plane of the preliminary radiation image, locations on the outer contours of the measurement object that are farthest apart from the axis of rotation on both sides of the axis of rotation are equidistant from the axis of rotation.

2. The measuring arrangement according to claim 1, wherein the invasive radiation is X-ray radiation.

3. The measuring arrangement according to claim 1, which comprises a control device for controlling said setting device, and wherein the measuring arrangement is configured to automatically correct a position of the measurement object when locations of the outer contours of the measurement object lying at a greatest distance, are not located equidistant from the axis of rotation.

4. The measuring arrangement according to claim 1, wherein said radiation source is configured to generate a conical diverging radiation beam emitted in a direction of said detection device.

5. The measuring arrangement according to claim 4, wherein a central ray of the conical radiation beam crosses the axis of rotation of said rotating device perpendicularly.

6. The measuring arrangement according to claim 1, wherein said setting device of said positioning device includes at least one positioning unit configured to set a position of the measurement object only along a rectilinear axis.

7. The measuring arrangement according to claim 6, wherein said setting device includes at least two said positioning units, and the rectilinear axes of the respective said positioning units run transversely to one another.

8. The measuring arrangement according to claim 7, wherein said setting device includes three said positioning units, and the rectilinear axes of the respective said positioning units run orthogonally relative to one another.

9. The measuring arrangement according to claim 1, wherein said setting device is electrically actuated, and wherein at least one electric line is provided for supplying said setting device with electric current, and an electric connection that connects a first part of the line disposed in and/or on said rotating device to a second part of the line disposed in and/or on said positioning device.

10. The measuring arrangement according to claim 1, wherein said setting device is electrically actuated, and wherein at least one electric line is provided for supplying said setting device with electric current, said electric line leading via at least one electric sliding contact configured to enable a movement of at least one part of said positioning device relative to another part thereof and/or relative to said rotating device while maintaining electric contact.

11. A method of carrying out computed tomography, the method which comprises:

transradiating a measurement object with invasive radiation in a variety of rotary positions with reference to an axis of rotation of a rotating device and each time recording at least one radiation image, and adjusting a relative position of the measurement object relative to the axis of rotation of the rotating device by adjusting a positioning device;

generating detection signals with a detection device and forming radiation images from the detection signals;

prior to recording radiation images to be used for evaluating the measurement object, taking at least one preliminary radiation image of the measurement object;

determining, in the preliminary radiation image, an image position of the axis of rotation corresponding to a radiation projection of the axis of rotation onto the detection device; and evaluating the at least one preliminary radiation image for determining whether or not, in one image plane of the preliminary radiation image, locations on the outer contours of the measurement object that are farthest apart from the axis of rotation on both sides of the axis of rotation are equidistant from the axis of rotation.

12. The method according to claim 11, which comprises irradiating the measurement object with X-ray radiation.

13. The method according to claim 11, which comprises centering the measurement object relative to the axis of rotation prior to recording the radiation images.

14. The method according to claim 11, which comprises mounting a part of the positioning device in a stationary fashion relative to the axis of rotation.

15. The method according to claim 11, which comprises automatically correcting the position of the measurement object by controlling the positioning device when the locations on the outer contours of the measurement object lying at a greatest distance on the two sides of the axis of rotation are not disposed equidistant from the axis of rotation.

\* \* \* \* \*